United States Patent [19]

Stanley et al.

[11] Patent Number: 4,746,612

[45] Date of Patent: May 24, 1988

[54] AOTUS INTERSPECIES HYBRIDOMAS AND MONOCLONAL RECEPTORS PRODUCED THEREBY

[75] Inventors: Harold A. Stanley, La Jolla; Robert T. Reese, San Diego, both of Calif.

[73] Assignee: Scripps Clinic & Research Foundation, La Jolla, Calif.

[21] Appl. No.: 660,478

[22] Filed: Oct. 12, 1984

[51] Int. Cl.$^4$ .................. C12N 5/00; C12N 15/00; C07K 15/04

[52] U.S. Cl. .................. 435/240.27; 435/68; 435/70; 435/172.2; 935/96; 935/100; 935/103; 935/102; 530/350; 530/387; 530/388

[58] Field of Search ............ 435/68, 70, 172.2, 240, 435/241; 935/96, 102, 100, 103; 530/350, 387, 388

[56] References Cited

U.S. PATENT DOCUMENTS 4,466,917  8/1984  Nussenzweig .................. 435/68

OTHER PUBLICATIONS

Holder, A. A. et al., J. Exper. Medicine 156:1528–1538 (11-1982).
Reese, R. T. et al., Am. J. Trop. Med. Hyg. 30:1168–1178 (1981).
Holder, A. A. et al., J. Exper. Medicine 160:624–629 (8-1984).
Kearney, J. F. et al., J. Immunology 123:1548–1550 (10-1979).
Buck, D. W. et al., *Monoclonal Antibodies and Functional Cell Lines*, R. H. Kennett et al., eds., Plenum Publ. (1984), pp. 275–309.

*Primary Examiner*—Margaret Moskowitz
*Attorney, Agent, or Firm*—Dressler, Goldsmith, Shore, Sutker & Milnamow, Ltd.

[57] ABSTRACT

*Aotus trivirgatus* interspecies hybridomas, their monoclonal receptors and methods of preparation and use are disclosed. The hybridomas are prepared by fusion of Aotus antibody-producing cells with myeloma cells containing about an equal number of chromosomes per cell. The resulting hybridomas are stable and secrete Aotus receptors. Particular receptors that immunoreact with antigenic proteins of *Plasmodium falciparum* shizonts and merozoites are disclosed.

34 Claims, No Drawings

AOTUS INTERSPECIES HYBRIDOMAS AND MONOCLONAL RECEPTORS PRODUCED THEREBY

DESCRIPTION

The U.S. Government has certain rights in this invention pursuant to a grant from the Agency for International Development.

TECHNICAL FIELD

This invention relates to interspecies hybridomas, and more particularly to *Aotus trivirgatus*-derived hybridomas and monoclonal receptor (immunoglobulin) molecules produced therefrom, including Aotus-derived monoclonal receptors that react with non-viral parasite antigens procuced by a human parasite.

BACKGROUND

In 1975 Kohler and Milstein showed that somatic cell hybridizations could be used to establish continuous cell lines capable of secreting specific antibodies against predefined antigens. The antibodies produced by such cell lines are fundamentally different from polyclonal antisera obtained from conventionally immunized mammals. Each such cell line or hybridoma produces a homogeneous, or monoclonal, immunoglobulin that represents only one of the many antibodies produced by the immunized mammal. Thus, a perpetual supply of antibody of predetermined specificity may be created. Kohler, G. and Milstein, C. (1975) *Nature* 256:495-497.

The classic hybridoma technique is based on the fusion of mortal antibody-prooucing B lymphocytes from an immunized animal with immortal cells derived from a myeloma cell line. In usual practice, the myeloma cell line does not itself produce antibooies. When the non-producing variant (myeloma) for immunoglobulin production is fused with the antibody-producing cell such as a B lymphocyte, immunoglobulin production is not extinguished, nor is production (secretion) of immunoglobulin by the myeloma reactivated. Hybrids produced only those immunoglobulin chains that were being produced by the parental cells at the time of fusion.

The monoclonal antibodies produced by hybridomas have been widely used to elucidate the antigenic structure of viruses. These studies have focused attention on the potential of vaccination and the role of immunity in parasitic diseases. Yet study of protozoan parasites has been difficult because of the complex life cycle of these organisms. Since production of hybridomas does not require purified antigen, monoclonal antibodies offer a simple and attractive approach to the study of human parasitic disease.

As described by Potocnjak, P., et al., (1980) *J. Exp. Med.* 151:1504-13, and Yoshida, N., et al., (1980) *Science* 207:71-73, for the spozozoite of malaria, monoclonal antibodies against different antigens can be screened to determine which one confers protection, and that specific monoclonal antibodies can be used to purify the surface antigen and produce a vaccine. Monoclonal antibodies have been generateo against a number of parasites whose biochemistry and mechanism of pathogenesis can now be more quickly explored. Pearson, T. et al., (1980) *J. Immunol. Methods* 34:141-54; Sethi, K. et al., (1980) *J. Parasitol.* 66:192-96.

In most cases, the hybridomas producing these monoclonal antibodies have been obtained by the fusion of mouse myelomas and antigen-stimulated mouse lymphocytes isolated from the spleen. While useful to a certain extent in antigenic analyses, monoclonal antibodies of rodent origin directed against human parasites suffer at least two shortcomings. First, rodents do not necessarily respond to the same antigenic determinants of the parasite as do humans. See Sikora, K. and Wright, R. (1981) *Br. J. Cancer* 43:696-700. Second, rodent monoclonal antibodies would have limited use in human immunotherapy because they are viewed by the human immune system as foreign, and are rejected. Olsson, L. and Kaplan, H. (1980) *Proc. Natl. Acad. Sci. USA* 77:5429-5431.

Attempts at overcoming the above-described shortcomings have focused on hybridizing antigen stimulated human lymphocytes with either human or mouse myelomas. The production of human-human intraspecies hybridomas has been hampered mainly by the current scarcity of human myeloma cell lines, which when fused, will support the production of immunoglobulin. Kozbor, D. and Roder, J. (1983) *Immunol. Today* 4:72-79. In addition, there are constraints on how the lymphocytes of humans can be ethically stimulated and obtained.

To overcome the lack of human-derived cell fusion partners, human lymphocytes have been fused with mouse myeloma cell lines to yield mouse-human interspecies hybrids. Such hybridomas have been made to secrete human antibody against the Forssman antigen [Nowinski, R. et al., (1980) *Science* 210:237-239], human mammary carcinoma cells [Schlom, T. et al., (1980) *Proc. Natl. Acad. Sci. USA* 77:6841-6845], keyhole limpet hemocyanin [Lane, H. et al., (1982) *J. Exp. Med.* 155:333-338] and tetanus toxoid [Kozbor, D. et al., (1982) *Hybridoma* 1:323-328].

However, it has been found that most mouse-human interspecies hybridomas preferentially segregate human chromosomes, thereby making preparation of stable lines secreting human antibody a labordous task. Such loss of human chromosomes from mouse-human hybridomas is not random. It is known that human chromosomes 14 (heavy chain) and 22 (light chain-lambda) are preferentially retained whereas chromosome 2 (light chain-kappa) is preferentially lost.

Even hybrids possessing the appropriate human chromosomes often fail to secrete human immunoglobulin because the appropriate environmental stimuli are absent. Kozbor, D. and Roder, J., supra. In addition, mouse-human hybrids that do produce antibodies are reported to secrete mouse immunoglobulins and/or immunoglobulins that are part mouse and part human. Schwaber, J. (1975) *Exp. Cell Res.* 93:343-354.

U.S. Pat. Nos. 4,172,124 and 4,196,265 to Koprowski et al. disclose the production of monoclonal antibodies that immunoreact with tumors and viruses, respectively. Both patents teach that the species from which the antibody-producing cell and myeloma cell are derived are unimportant to the production of the resulting, fused hybridoma cells. Those teachings nothwithstanding, those patents only specifically disclose the preparation of mouse-mouse hybridomas, and those skilled in the art are aware that the species of the lymphocyte and myeloma cell lines are important to the successful production of useful hybridomas and of their monoclonal antibodies.

The present invention, described hereinafter, resulted from study of parasitic microorganisms of the genus Plasmodium. The genus is currently defined on the basis of one type of asexual multiplication by division occurring in the parenchymal cells of the liver of the vertebrate host (exo-erytahrocytic schizogony); the other characteristic is that the mosquito host is a species of Anopheles. L. J. Bruce-Chwatt. *Essential Malariology*, William Heinemann Medical Books, Ltd., London (1980) Chapter 2. The four generally recognized species of *Plasmodia* infecting man are *P. malariae, P. vivax, P. falciparum* and *P. ovale.*

The life cycle of all species of human malaria parasites is essentially the same. It comprises an exogenous sexual phase (sporogony) with multiplication in certain Anopheles mosquitos, and an endogenous asexual phase (schizogony) with multiplication in the vertibrate host. The latter phase includes a developmental cycle in the red corpuscles in the blood (erythrocytic schizogony) as well as the cycle taking place in the parenchymal cells of the liver (exo-erythrocytic schizogony).

In the early phases of erythrocytic schizogony, the parasites are termed trophozoites. After a period of growth the trophozoites multiply by the asexual dividing process of schizogony. Mature schizonts are fully developed forms in which, as a result of the segmentation of the nucleus and the cytoplasm, a number of small rounded forms termed merozoites are produced.

When the process of schizogony is completed, the red blood cell bursts and the merozoites then invade fresh erythrocytes in which another generation of parasites is produced by the same process. This process is repeated over and over again in the course of infection leading to a progressive increase of parasitemia until the process is slowed down by the host's immune response.

Of all the species of human Plasmodia, *P. falciparum* is the most highly pathogenic. A *P. falciparum* infection in non-immune subjects usually runs an acute course, and frequently terminates fatally unless promptly treated with specific drugs.

Currently, the only certain means of diagnosing malarial infection is the detection of the Plasmodium by microscopical examination of the blood. The thick film method is recommended because it concentrates by a factor of 20–40 the layers of red blood cells on the microscope slide surface, and thereby reveals even scanty infections within a short time. While the parasites are easily detected in the thick film assay, they are very difficult to identify as to species using this method.

Since species identification may be clinically important, the thick film assay must be supplemented by a thin film assay that allows for species identification. Standard practice requires that an experienced technician examine an appropriately stained thick film for at least 5 minutes (corresponding to approximately 100 microscopic fields under oil immersion); thin films must be examined for 15–20 minutes before a negative report is justified. In doubtful cases repeated blood films must be taken and examined every 4 hours, resulting in a significant investment of technician time. The thick and thin film methods are described by L. J. Bruce-Chwalt in *Essential Malariology*, William Heinemann Medical Books, Ltd., London (1980) pages 76–96.

Assays using immunofluorescence, immuno-haemagglutination, immuno-precipitation and enzyme-linked immunosorbent methods have been used widely for the detection and measurement of anti-malarial antibodies. However, these serological tests are of limited use for the diagnosis of acute malaria since they become positive only several days after the appearance of malarial parasites in the blood.

Once malaria has been diagnosed there exists a spectrum of antimalarial drugs that may be used to intervene on different phases of the parasite life cycle. The state of the infected person's immunity has a bearing on the use of drugs since persons who have acquired a degree of immunity through exposure can be cured or protected from serious symptoms more easily than those who have not. However, to date there is no drug available that provides absolute protection from initial infection.

Despite the remarkable progress in the study of immune responses in malaria there still exists no vaccine against the parasite. Natural immunity in malaria is directed against the asexual erythrocyte forms of the parasite (i.e., trophozoite, schizont ano merozoite), but not necessarily against sporozoites. However, further progress in this area has been hampered by the inability to produce antisera specific for host-recognized antigenic determinants unique to these life cycle stages.

BRIEF SUMMARY OF THE INVENTION

The present invention contemplates a process for preparing an *Aotus trivirgatus* interspecies hybridoma that secretes monoclonal receptor molecules that immunoreact with a preselected antigen such as the non-viral, parasite antigenic glycoprotein having a molecular weight of about 185 kd produced by *Plasmodium falciparum* shizonts that is processed into polypeptide fragments during merozoite development. The process includes the steps of collecting antibody-producing cells such as splenocytes or peripheral B lymphocytes from an *Aotus trivirgatus* monkey immunized by the preselected antigen, e.g., *P. falciparum*. Those cells are then fused with myeloma cells from another animal type (non-Aotus) that contain about the same number of chromosomes per cell as do the Aotus antibooy-producing cells, e.g., within about 5 chromosomes per cell, to form hybridomas; the fusion taking place in the presence of a cell fusion promoter. The fusion is typically carried out with equal numbers of both types of cells.

The hybridomas so formed are cloned (plated and grown) in a culture medium that is selective for hybridoma growth, at a concentration of about 32 to about $2 \times 10^4$ cells per 200 microliters of medium, and more preferably at about $4 \times 10^3$ to about $2 \times 10^4$ cells per 200 microliters of medium. The cloned hybridomas are assayed and selected for the ability to secrete receptor molecules that immunoreact with the preselected antigen. A hybridoma that secretes such receptor molecules; i.e., a selected hybridoma, is thereafter subcloned to monoclonicity. The selected, subcloned hybridoma is cultured, and is collected. The monoclonal receptors of this invention that are secreted by the cultured hybridoma are recovered from the culture medium.

Particularly preferred hybridomas tnat secrete the receptor molecules of this invention are prepared by fusion of *Aotus trivirgatus* monkey cells that secrete antibodies to a preselected antigen such as *P. faciparum* with mouse myeloma cells from a non-secreting myeloma line such as the cell line denominated P3X63Ag8.653. Cells from *Aotus trivirgatus* monkeys of Karyotypes II and VI are reported to contain 54 and 56 chromosomes, respectively. Cells from the above myeloma line are reported to contain 58 chromosomes.

A hybridoma cell line is also contemplated herein. That cell line is prepared by the fusion of antibody-producing cells from *Aotus trivirgatus* with myeloma cells from another animal type (non-Aotus) that contain about the same number of chromosomes per cell. The myeloma cell line is preferably a non-secreting line such as mouse myeloma line P3X63Ag8.653.

The hybridoma cell line, when cultured, secretes monoclonal receptor molecules for at least six weeks after cloning. Those receptor molecules: (a) are biologically active; i.e., they immunoreact with a preselected antigen ligand such as that with which antibodies from the fused Aotus cells immunoreacted, (b) are bound by polyclonal antibodies raised to antibodies of *Aotus trivirgatus;* and (c) are not substantially bound by polyclonal antibodies raised to antibodies of the animal type from which the myeloma cells are obtained, e.g., antibodies to mouse antibodies where a mouse myeloma line is used.

Preferred receptor molecules are also bound by polyclonal antibodies raised to human antibodies.

The antigen that immunoreacts with (is bound by) the before-mentioned antibodies from Aotus antibody-producing cells and with the Aotus monoclonal receptors of a particularly preferred hybridoma is a protein, including a glycoprotein, of *Plasmodium falciparum.* Most particularly, that antigen is a glycoprotein having a molecular weight of about 185 kd by SDS-PAGE that is made by *P. falciparum* shizonts and is processed into polypeptide fragments during *P. falciparum* merozoite development.

Four particularly preferred hyridoma cell lines of this invention were received by the American Type Culture Collection on Oct. 11, 1984. Those hybridomas are denominated: F18-P3-10G SCRF 63.0 (ATCC HB 8641); F18-P2-10E SCRF 63.0 (ATCC HB 8640); F19-P9-11B SCRF 63.0 (ATCC HB 8642): and F19-P21-9C SCRF 63.0 (ATCC HB 8643).

The present invention further contemplates hybridoma-secreted monoclonal receptors. Those receptors: (a) are biologically active; (b) are bound by polyclonal antibodies raised to antibodies of *Aotus trivirgatus;* and (3) are not substantially bound by polyclonal antibodies raised to non-Aotus antibodies of the same animal type from which the myeloma cells were obtained, e.g., antibodies to mouse antibodies.

Preferred receptors are biologically active in that they immunoreact with a preselected, non-viral, parasite antigen protein such as a protein of *Plasmodium falciparum* shizonts or merozoites. In more preferred embodiments the receptors bind to a 185 kd glycoprotein produced by *P. falciparum* shizonts that is processed into polypeptide fragments during merozoite development. Still more preferably, the receptors bind to the 185 kd glycoprotein as well as to one or the other of two groups of the polypeptides into which the 185 kd glycoprotein is processed by the *P. falciparum* merozoites. The most particularly preferred receptors also bind to one or more of the Honduras, Kenya, Indochina, Geneva and Kenya strains of *P. falciparum.*

DETAILED DESCRIPTION OF THE INVENTION

I. INTRODUCTION

One enormous advantage of hybridoma technology is its ability to generate antibodies of predetermined specificity even with impure antigens. Viewed from this perspective, the use of hybridoma technology to produce monoclonal antibodies may be considered an antibody purification process.

When an animal is immunized with an immunogen (antigen), its immune system produces a repertoire of lymphocytes, each producing only one antibody molecule. The serum of such an animal therefore contains many different antibodies directed against the immunogen; i.e., the antibodies are polyclonal. If the immunogen was impure, many irrelevant antibodies will also have been induced and are contained in the serum.

The hybridoma technique of prooucing antibodies clones one antibody-forming cell away from all others present in the immunized animal's antibody-producing cell repertoire. Cells that secrete antibodies reacting to impurities are discarded during the initial screening process. The monoclonal cell cultures so isolated produce only one antibody that is homogeneous in chemical composition, contains only one binding site idiotype and displays only one binding affinity for its corresponding antigenic determinant.

The ability to secrete mono-specific antibodies directed against those immunogenic determinants naturally recognized by the host of a parasitic infection would be a great boon to diagnostic and clinical efforts. Prior to the present invention, preparation of such antibodies was not practicable because an efficient fusion system capable of ethical manipulation was not available.

The words "secrete" and "produce" are often used interchangably in the art as to cells from which antibody molecules are obtained. Cells that produce antibodies may, however, not secrete those molecules into their environment. The cells of interest herein secrete the antibodies into their environment. Nevertheless, such cells are referred to herein as "antibody-producing" cells in keeping with the phrase utilized in the art.

In the case of human malaria, it is known that a substantial portion of the host's immune response is directed against the merozoite. Immunity against the merozoite that causes the disease's clinical symptoms can be passively transferred with immune gamma globulin. Cohen, S., et al., (1961) *Nature* 192:733-735. For vaccine development, therefore, it is important to identify and characterize the surface antigens of merozoites against which human protective antibodies may be directed.

The composition of the merozoite plasma membrane is only now being explored. Recent studies have shown that the processing products of a 185 kilodalton (kd) glycoprotein, sometimes reported as a 190 kd or 195·kd protein, contain antigenic determinants recognized by an infected host. However, those results were obtained in rodent systems. While they identify the major protein antigens for rodent immunity, they do not necessarily identify those specific determinants important in human immunity.

The present invention provides an exemplary, model system for the study of malaria that closely resembles the natural human system. A simian system was chosen because of the close phyletic relationship between monkeys and man. In addition, such a system has less stringent ethical constraints in terms of immunization through infection with live parasites.

In the present study, the simian species *Aotus trivirgatus* was chosen as parasite host because of its ability to be infected by the human malarial parasite *P. falciparum.* It is believed that such an infection induces an immune response in the simian host that is very similar to a human response to malaria. See Reese, R. et al. (1981) *Am. J. Trop. Med. Hyg.* 306:1168-1178.

A. Aotus Interspecies Hybridomas

The present invention contemplates a stable hybridoma cell line that secretes immunological receptor molecules and comprises a cell hybrid of a simian, Aotus, antibody-producing cell fused to a non-Aotus myeloma cell having about the same number of chromosomes as does the Aotus cell; i.e., within about 5 chromosomes of the same number per cell. The hybridoma so produced contains genetic material of both Aotus and non-Aotus origin that can be identified by DNA hybridization techniques. A hybridoma so prepared secretes monoclonal receptor molecules that are biologically active in that they immunoreact with an antigen such as a non-viral, parasite antigen like an antigen expressed on the surface of a P. falciparum merozoite.

The monoclonal receptor molecules secreted by the hybridoma are Aotus receptors and are bound by polyclonal antibodies raised to Aotus antibooies. Those receptors are not bound by polyclonal antibodies raised to antibodies from the same animal type from which the myeloma cell used in the fusion was obtained. Thus, the monoclonal receptors secreted by the particularly preferred hybridomas of this invention are bound by anti-Aotus monkey Ig antibodies, but are not bound by anti-mouse Ig antibodies. It has also been found that the monoclonal receptors of the particularly preferred hybridomas of this invention are bound by anti-human Ig antibodies.

A hybridoma of the present invention is also stable. By "stable" it is meant that the hybridoma secretes its monoclonal receptor for a period of at least six weeks after cloning, when grown in culture medium.

The Aotus monkeys have about the same number of chromosomes per cell; i.e, within about 5 chromosomes, as do the cells of the myeloma cell line with which they are fused to form the hybridoma. For example, A. trivirgatus Karyotype II and Karyotype VI are reported to have 54 and 56 chromosomes, respectively. [Ma, N. et al. (1976) Lab. Anim. Sci. 26:1022–1036.] An exemplary mouse-derived myeloma with which the Aotus antibody-prooucing cells are fused (P3X63Ag8.653) is reported to contain 58 chromosomes. [*Hybridoma Techniques*, EMBO SKMB Course, 1980, Basel, Cold Spring Harbor, N.Y. (1980), page 8.]

While not wishing to be bound by any single theory, it is believed that the approximate matching of chromosome numbers between the cell fusion partners is in large part responsible for the stability of the interspecies cell fusions of this invention.

Exemplary emodiments of the hybridomas of this invention were produced in two separate fusions (fusions F18 and F19) using in vivo antigenically stimulated B lymphocytes isolated from the spleen of owl monkey Aotus 127 (Karyotype II) that was previously immunized against P. falciparum.

The hybridomas produced in F18 and F19 were cloned (plated and grown), and initially screened for receptor molecule secretion using an immunofluorescent antibody technique (IFAT). This technique, described in detail in the materials and methods section II(E), is a modification of the thin film clinical diagnostic technique.

Briefly, in this technique, any antibodies secreted were assayed for their ability to immunoreact with merozoites in infected erythrocytes spread on a microscope slide. The presence of an imunoreaction between the secreted antibodies and the merozoites was detected by admixture with second, fluorescing antibodies that bound to the antibodies that immunoreacted with the merozoites.

Some of the hybridomas from F18 and F19 secreting receptor molecules that had initial positive titers of 3 or greater in the IFAT are listed in Table 1 below. This initial screening assay allowed for the selection of hybridomas secreting desired antibodies from those secreting irrelevant antibodies or none at all. Many of the IFAT-positive hybridomas were then subcloned to monoclonality; those with unknown clonicity are underlined in Table 1. Those hybridomas producing monoclonal antibodies of desired antigen specificity; i.e., those secreting monoclonal receptors that immunoreacted with P. falciparum merozoites, were recovered.

The monoclonal hybridomas in Table 1 that have American Type Culture Collection (ATCC, 12301 Parklawn Drive, Rockville, Md. 20852) accession numbers are among the particularly preferred embodiments of this invention.

TABLE 1

| Cell Hybrids of *Aotus Splenocytes* Fused to Mouse Myeloma Cells | | |
|---|---|---|
| Hybridoma Designation* | IFAT Titer** | ATCC Accession Number |
| F18-P4-3D | 3 | |
| F18-P3-5C | 81 | |
| F18-P3-10G | 81 | HB 8641 |
| F18-P1-7B | 81 | |
| F18-P2-10E | 81 | HB 8640 |
| F18-P2-7C | 27 | |
| F19-P5-11D | 9 | |
| F19-P21-9C | 81 | HB 8643 |
| F19-P1-3E | 81 | |
| F19-P2-5E | 81 | |
| F19-P12-7D | 81 | |
| F19-P9-11B | 81 | HB 8642 |
| F19-P12-3G | 9 | |
| F19-P13-7D | 81 | |
| F19-P20-3E | 81 | |
| F19-P22-5E | 3 | |
| F19-P1-2G | 3 | |
| F19-P10-4F | 27 | |
| F19-P18-11E | 3 | |
| F19-P18-10B | 3 | |
| F19-P12-4G | 27 | |
| F19-PG-8F | 81 | |
| F19-P11-9D | 9 | |
| F19-P1-3B | 81 | |
| F19-P14-8B | 81 | |
| F19-P21-11F | 9 | |
| F19-P17-GE | 27 | |

*Underlined hybridoma designations indicate unknown clonicity of the hybridomas.
**IFAT = Immunofluorescent antibody test, as described in materials and methods, section II, E.

A hybridoma cell line of this invention secretes monoclonal antibodies that are referred to herein as receptor molecules. In fact, the secretion of Aotus-derived receptor molecules is a distinguishing characteristic of the hybridomas of this invention. This characteristic allows them to be identified, isolated and subcloned to monoclonality.

A receptor is a biologically active molecule that immunologically binds to (reacts with) a ligand. The receptor molecules of this invention contain an idiotype (antibody combining site), and are intact antibodies, substantially intact antibodies, or idiotype-containing polypeptide (combining site) portions of antibodies.

Biological activity of a receptor molecule is evidenced by the binding of the receptor to its antigenic ligand or antigen upon their admixture in an aqueous medium, at about physiological pH values and ionic strengths. Preferably, the receptors also bind to the antigenic ligand within a pH value range of about 5 to about 9, and at ionic strengths such as that of distilled water to that of about one molar sodium chloride.

Idiotype-containing polypeptide portions (antibody combining sites) of antibodies are those portions of antibody molecules that include the idiotype and bind to an antigenic ligand such as a merozoite, and include the Fab and F(ab')$_2$ portions of the antibodies. Fab and F(ab')$_2$ portions of the antibodies are well known in the art, and are prepared by the reaction of papain and pepsin, respectively, on antibodies by methods that are well known. See for example, U.S. Pat. No. 4,342,566 to the Theofilopolous and Dixon. Intact antibodies are preferred, and will be utilized as illustrative of the receptor molecules contemplated by this invention.

The term "antigen" as used herein, means an entity that is immunologically bound by a receptor molecule.

The term "immunogen", as used herein describes an entity that induces antibody production in the host animal. In some instances, the antigen and immunogen are the same entity, while in other instances, the two entities are different. Where the immunogen and antigen are the same entity, the term antigen is used herein.

The term "antigenic determinant", as used herein, designates the structural component of a molecule that is responsible for specific interaction with corresponding receptor molecules (immunoglobulin) elicited by the same or related antigen or immunogen.

The term "immunogenic determinant", as used herein, designates the structural component of a molecule (the epitope) that is responsible for the induction in a host of a receptor molecule containing an idiotypic, antibody combining site that binds with the immunogen when used as an antigen.

The present invention contemplates a process of preparing a stable, interspecies hybridoma cell line and monoclonal receptor molecules therefrom. In the present invention, the exemplary receptor molecules of particularly preferred embodiments react with a protein, including a glycoprotein, of a P. falciparum shizont or merozoite. However, it is to be understood that the method of the present invention for preparing stable, interspecies hybridomas and their monoclonal receptors is general, ano is not limited to the preparation of the hybridomas and receptor molecules shown herein by way of example.

The process of preparing the hybridoma begins by collecting antibody-producing cells from an Aotus monkey immunized to a preselected antigen. The useful antibody-producing cells (B lymphocytes) are typically splenocytes obtained by spleenectomy or are peripheral B lymphocytes that may be obtained from the blood as by vena puncture. Lymph node and bone marrow cells can also serve as the source of B lymphocytes.

The collected antibody-producing cells secrete antibodies to a preselected antigen. In the exemplary procedures described herein, the Aotus was actively immunized by infecting the animal with P. falciparum. Immunization by infection is preferable, but is not thought to be necessary to the success of the present method. Thus, P. falciparum provides the preselected antigens used herein. However, vaccination utilizing a regimen as is known in the art also is useful in this process.

The collected antibody-producing cells are then fused with cells of non-Aotus myeloma cells that contain about the same number of chromosomes per cell as do the Aotus cells. That is, the collected Aotus cells and the myeloma cells used for fusion each contain a diploid chromosome number that is within about five of the other cell.

For example, where cells of an Aotus trivirgatus of Karyotype II (54 diploid chromosomes) are the antibody-producing cells, they may be fused with myeloma cells containing about 49 to about 59 diploid chromosomes. Similarly, cells of an Aotus trivirgatus of Karyotype VI (56 diploid chromosomes) may be fused with myeloma cells containing about 51 to about 61 chromosomes.

The myeloma cells are from an animal other than an Aotus monkey. Preferably, the myeloma cells are non-secreting. A particularly preferred myeloma cell that is useful for fusions with Aotus of either Karyotype II or Karyotype VI is the non-secreting mouse myeloma cell line denominated P3X63Ag8.653 (ATCC CRL 1580) that is reported to have 58 chromosomes, as noted before.

The cell fusion is typically carried out at a ratio of antibody-producing cells to myeloma cells of about 1:1. An excess of the myeloma cells up to about 10 fold may also be used.

The cell fusion is carried out in the presence of a cell fusion promoter. Such materials include Sendai virus, polyethylene glycol of an average molecular weight of about 500 to about 2000, or an electric current as is well known.

The fused cells are thereafter cloned (plated and grown) in a culture medium that is selective for hybridoma growth such as the HAT medium utilized herein. The cloning is broadly carried out at a concentration of about 32 to about 20,000 ($2 \times 10^4$) cells per 200 microliters.

The cloned hybridomas are assayed and selected for the ability to secrete receptor molecules that immunoreact with the preselected antigen. The IFAT assay described herein is one such useful assay. The particular assay utilized is typically a function of the antigen and receptor molecule system, and is not a feature of this invention.

A hybridoma that secretes receptors of the desired specificity; i.e., a selected hybridoma, is thereafter subcloned to monoclonicity as is known in the art. The subcloned, monoclonal hybridoma is then cultured and may be recovered as desired.

In more preferred practice, the Aotus antibooy-producing cells are frozen, and then thawed immediately prior to the before-described, hybridoma-forming, fusion step of the hybridoma preparation process. By "immediately" it is meant that the thawed cells are fused as quickly as possible after thawing because such cells typically die quickly in culture medium.

A still more preferred process of preparing hybridoma further comprises the step of enriching the lymphocytes for receptor production prior to lymphocyte collection. The enriching process may be carried out within about one week, and more preferably within about 3 days, of lymphocyte collection for fusion by in vivo antigenic stimulation or in vitro antigenic stimulation. Specific examples of in vivo and in vitro antigenic stimulation are found in materials and methods sections II(B) 2 and 3, while a more general discussion may be found hereinafter.

The monoclonal receptors of this invention may be obtained by culturing a hybridoma of this invention, and collecting the secreted receptor molecules from the supernatant growth medium. As already noted, the monoclonal receptor molecules are biologically active in that they immunoreact with a preselected antigen ligand such as the antigen ligand with which the antibodies of the Aotus antibody-producing cells reacted.

For example, the Aotus monkeys utilized herein were actively immunized against *P. falciparum*, and their antibodies immunoreacted with a protein of a *P. falciparum* shizont or merozoite such as the before-mentioned 185 kd glycoprotein. The particularly preferred hybridomas prepared by fusion of antibody-producing cells of those immunized monkeys also immunoreacted with a protein of *P. falciparum* shizont or merozoite.

The monoclonal receptor molecules of this invention that are secreted by a hybridoma of this invention are bound by polyclonal antibodies raised to antibodies of *Aotus trivirgatus*. Thus, for example, the receptor molecules of this invention are bound by rabbit anti-Aotus Ig antibodies.

Conversely, the monoclonal receptor molecules of this invention that are secreted by a hybridoma of this invention are not substantially bound by polyclonal antibooies raised to antibodies of the animal type from which the myeloma cells are derived. For example, where mouse myeloma P3X63Ag8.653 cells are used in the fusion, goat anti-mouse Ig antibodies do not immunoreact in the IFAT assay with the secreted receptors of the present invention.

Put differently, the receptor molecules of this invention: (1) are receptors for a preselected antigen ligand such as the antigenic ligand molecules used to immunize the Aotus monkey; (2) are ligands for anti-Aotus Ig polyclonal antibodies; and (3) are neither substantial ligands nor receptors for polyclonal antibodies raised to antibodies of the animal type of the myeloma line, although minor, generalized antibody-antibody reactions may occur.

The monoclonal receptor molecules are also bound by (ligands to) antibodies raised to human antibodies.

In the series of studies described herein, the hybridomas are the product of fusion of an *Aotus trivirgatus* antibody-producing cell and mouse myeloma cell P3X63Ag8.653. The receptors produced by such embodiments are whole antibodies that are bound by polyclonal antibodies raised to Aotus antibodies, are not bound by antibodies raised to mouse antibodies, and more preferably, are also bound by polyclonal antibodies raised to human antibodies.

The method of hybridoma preparation used in the present study takes advantage of the fact that Aotus species monkeys can be infected with the non-viral parasite *P. falciparum*. Upon drug treatment, the infected monkeys develop a solid, active immunity; i.e., innoculations of normally lethal parasite doses result in little or no detectable parasitemia.

In addition, the use of the Aotus monkey as a source of antibody-producing cells such as B lymphocytes for the production of hybridomas has several advantages over the use of humans as such a source. The monkeys can be infected repeatedly with the pathogen until a high degree of active immunity is obtained. Adjuvants such as Freund's, that are unacceptable for use in humans can be used in the monkeys to improve the immune response to immunogens. Third, the monkeys can be readily spleenectomized.

The process of the present invention contemplates two previously noted, distinct, particularly preferred embodiments that include the step of enriching lymphocytes for receptor molecular production. In one embodiment, the Aotus splenic B lymphocytes were enriched for receptor production by in vivo antigenic stimulation. In the other, enrichment of peripheral blood lymphocytes was accomplished by in vitro stimulation.

The results of two fusions, each using one of the enrichment methods, are shown in Table 2, below. In fusion A, the lymphocytes were enriched by in vivo antigenic stimulation, and were subsequently recovered from the spleen as described in the material and methods section II(B)2. In fusion B, the peripheral blood lymphocytes (PBL) were enriched by in vitro stimulation as is discussed in materials and methods section II(B)3. Also shown in Table 2 are the results of a mouse-mouse fusion shown for comparative purposes.

TABLE 2

| | Monkey Fusions | | |
| --- | --- | --- | --- |
| | in vivo Stimulation (A) | in vitro Stimulation (B) | Mouse Fusion |
| splenocytes | $7 \times 10^6$ | — | $2 \times 10^8$ |
| PBL | — | $1 \times 10^7$ | — |
| wells seeded | 1380 | 640 | 2400 |
| myeloma or lymphocyte cells/well | $5 \times 10^3$ | $1.5 \times 10^4$ | $8 \times 10^4$ |
| wells with hybrids | 1067 | 420 | 1563 |
| % wells with hybrids | 77 | 66 | 65 |
| antibody positive wells* | 97 | 40 | 278 |
| % antibody positive wells** | 9 | 10 | 18 |
| stable hybridomas | 14 | 3 | 156 |
| % stable hybridoms*** | 1 | 1 | 10 |
| Stable hybridomas/$10^6$ lymphocytes placed into wells for fusion | 2 | 0.3 | 0.78 |

*Number of wells in the 96 well plates containing antibody against either parasite or erythrocyte antigens.
**Number of antibody positive wells/number of wells with hybrids × 100.
***Number of stable hybridomas/number of wells with hybrids × 100.

Table 2 illustrates at least two unexpected advantages in using the methods contemplated by this invention to produce hybridomas.

First, the preferred in vivo enrichment method results in a fusion efficiency that is approximately 10 times higher than that obtained in a comparable mouse-mouse fusion. That result is particularly surprising in light of the report by Sikora and Wright, supra, that the fusion frequency for human-mouse and human-rat hybridization was much lower than that found using the same myeloma cells for a mouse-mouse or rat-rat hybridization.

Second, all of the stable Aotus-derived hybridomas poduced in this study secreted monoclonal antibodies reactive with *P. falciparum* merozoite surface antigens. In contrast, only 6 of 156 mouse-mouse hybridomas produced antibodies with a similar specificity. Of those 6 hybridomas, only 4 produced monoclonal receptors that reacted with merozoite surface antigens. This result is believed to be due to the monkey's immune response more nearly approximating that of a human, the parasite's natural host, than a mouse.

These advantages indicate that the Aotus hybridoma system of this invention will be useful in producing monoclonal antibodies reactive with other non-viral, human parasitic pathogens.

The results of fusion A shown in Table 2 were obtained by first performing a preliminary titration to establish an initial cell concentration that promoted growth of immunoglobulin producing hybrids but discouraged overgrowth of the producers by non-producing hybrids. Overgrowth was found to occur at the cell densitites normally used for mouse-mouse fusions. Cells from a fusion of $A.$ $trivirgatus$ splenocytes and mouse myeloma X63-Ag8.653 cells were plated, broadly, at concentrations of about 32 to about $2 \times 10^4$ cells per well (200 microliters of medium), and more preferably at about $4 \times 10^3$ cells to about $2 \times 10^4$ cells per 200 microliters of medium, in 96 well tissue culture microtiter plates (Costar, Model 3596, Cambridge, Mass.). The preferred concentration used for splenocytes was typically about one-third of that used for plating PBL.

It was determined that splenocyte cell concentrations of $2-10^4$ cells per well resulted in cell growth in virtually every well. Concentrations of $4-10^3$ splenocytes per well generally gave growth in 40-50% of the wells. Subsequent fusions using monkey splenocytes were initially seeded into plates at $4-5-10^3$ cells per well.

The results of fusion A indicate that 1067 of the 1380 wells initially seeded developed viable hybrids. Analyses by IFAT, discussed in detail in materials and methods section II(E), of the culture supernatants from these wells showed the presence of anti-merozoite antigen antibodies in 97 wells. As stated hereinbefore, none of the antibodies in these supernatants reacted with erythrocytes.

The hybrid cells in the IFAT-positive seed wells were then both subcloned to monoconality and subcultured to 24 well plates (Costar, Model 3524). When the supernatants from the 24 well plates were assayed by IFAT 11 days after subculturing, 61 wells no longer contained detectable amounts of anti-parasite antibodies (receptors).

This result is believed to be due to two factors. First, it is possible that some hybrids lose the ability to secrete immunoglobulin through an event such as gene loss. Second, it is known that imunoglobulin-producing cells replicate more slowly than non-producing cells. Therefore, it is likely that many producing hybrids were overgrown in the 24 well plates.

B. Receptor Molecules

The present invention also contemplates a monoclonal receptor molecule secreted by a hybridoma cell line of this invention. The receptor is preferably an intact antibody, as already noted. Particularly preferred monoclonal receptor molecules of this invention are discussed in this section.

As also noted earlier, the surface antigens of merozoites have only recently been studied using mouse monoclonal antibodies. These studies indicate that a 190 or 195 kilodalton (190-195 kd) antigenic glycoprotein is synthesized in $P.$ $falciparum$ schizonts, and is processed through a series of discrete polypeptide fragments during the last few hours of merozoite development. Since one of the processing products appears on the merozoite surface and is immunoprecipitated by human malaria-immune serum, the polypeptide products of the 190-195 kd protein are of considerable interest for malaria vaccine development. Freeman, R. R. and Holder, A. A., (1983) $J.$ $Exp.$ $Med.$ 158:1647-53.

In our laboratory, the reported 190-195 kd precursor was found to have an apparent relative molecular weight of 185 kd (185 kd) by SDS-PAGE. That protein will hereinafter therefore be referred to as a 185 kd glycoprotein.

Studies with mouse monoclonal antibodies indicate that the 185 kd precursor is processed into two antigenically distinct groups of polypeptides. Group 1 contains major polypeptides of apparent molecular weights of 120,000 (120 kd), 90,000 (90 kd), 88,000 (88 kd), 46,000 (46 kd) and 40,000 (40 kd). Group 2 contains major polypeptides of 152,000 (152 kd), 106,000 (106 kd) and 83,000 (83 kd).

The processed polypeptides of Group 2 (the 152 kd, 106 kd and 83 kd polypeptides) have been found to contain no detectable glucosamine, while the polypeptides of Group 1 (the 120 kd, 90 kd, 88 kd, 46 kd and 40 kd polypeptides) have been found to contain glycosylation.

Reports by others indicate that an 83 kd polypeptide is on the surface of the merozoite [Freeman, R. and Holder, A. (1983) $J.$ $Exp.$ $Med.$ 158:1647-1653; and Heidrich, H. et al. (1983) $Z.$ $Parasitenka.$ 69:715-725], whereas the 185 kd glycoprotein is not on the surface, and the 152 kd and 106 kd polypeptides may be altogether absent. Work from our laboratory with antibodies from mouse-mouse hybridomas (Howard and Reese, supra) indicates that the 46 kd or 40 kd polypeptides may be on the merozoite surface.

Receptor molecules in the form of intact antibodies secreted by hybridomas from fusions F18 and F19 were examined for their specificities with regard to merozoite antigens. The initial results, listed in Table 3, below, show a specificity for one or the other of the 185 kd precursor glycoprotein processing Groups 1 and 2 [RIPA results] as well as specificities among strains of $P.$ $falciparum$ (IFAT results). Each of the secreted monoclonal receptor molecules, except that secreted by the hybridoma designated F18-P2-10E, also immunoreacted with the 185 kd glycoprotein.

TABLE 3

| Hybridoma Designation | RIPA[6] | IFAT Malarial Strain | | | | |
|---|---|---|---|---|---|---|
| | | Hon[1] | Ken[2] | Indo[3] | Gen[4] | Tanz[5] |
| F18-P4-3D | 0 | * | * | * | * | * |
| F18-P3-5C | 0 | + | − | − | + | − |
| F18-P3-10G | 2 | + | − | − | + | − |
| F18-P1-7B | 1 | + | − | − | + | − |
| F18-P2-10E | 3** | − | + | + | + | − |
| F19-P5-11D | 2 | + | − | − | + | − |
| F19-P21-9C | 2 | + | + | + | + | + |
| F19-P2-5E | 0 | + | − | − | + | − |
| F19-P12-7D | 0 | + | − | − | + | − |
| F19-P9-11B | 1 | + | − | − | + | − |
| F19-P13-7D | 0 | * | * | * | * | * |
| F19-P20-3E | 0 | * | * | * | * | * |
| F19-P22-5E | 0 | * | * | * | * | * |
| F19-P10-4F | 0 | * | * | * | * | * |
| F19-P18-llE | 0 | * | * | * | * | * |
| F19-P12-4G | 0 | + | − | − | + | ± |
| F19-P6-8F | 2 | + | − | − | + | − |
| F19-P11-9D | 0 | + | − | − | + | + |
| F19-P1-3B | 2 | + | − | − | + | − |

TABLE 3-continued

Monoclonal Antibody Specificity and Strain Cross Reactivity

| Hybridoma Designation | RIPA[6] | IFAT Malarial Strain | | | | |
|---|---|---|---|---|---|---|
| | | Hon[1] | Ken[2] | Indo[3] | Gen[4] | Tanz[5] |
| F19-P17-6E | 2 | + | + | + | + | + |

[1]Hon = Honduras I/CDC (Central America) strain of *P. falciparum*.
[2]Ken = Kenya (East Africa) strain of *P. falciparum*.
[3]Indo = Indochina I (Vietnam) strain of *P. falciparum*.
[4]Gen = Geneva (Senegal West Africa) strain of *P. falciparum*.
[5]Tanz = Tanzania I (East Africa) strain of *P. falciparum*.
[6]RIPA = Radioimmune precipitation assay as described in the materials and methods section, and used to assay the polypeptide processing group with which the receptor immunoreacts. 0 = Only immunoprecipitation of the 185 kd glycoprotein was examined; 1 = Group 1; 2 = Group 2.
* = Not assayed.
** = Immunoreaction with a 35 kd protein and not with the 185 kd glycoprotein or with the polypeptides of either of Groups 1 or 2.
+ = Positive immunoreaction.
− = Negative immunoreaction.
± = Equivocal immunoreaction.

By way of illustration, the particularly preferred hybridoma F18-P3-10G secretes a receptor molecule that immunologically binds to (reacts with) the 185 kd precursor and to all three of the major Group 2 the processing products; i.e., the 152 kd, 106 kd and 83 kd polypeptides. Another particularly preferred hybridma, designated F19-P9-11B secretes receptors that immunoreact with the 185 kd precursor and each of the 120 kd, 90 kd, 88 kd, 46 kd and 40 kd polypeptide processing products of Group 1. The hybridoma designated F18-P2-10E secretes receptors that bind to a previously unknown polypeptide having a molecular weight of about 35 kd by SDS-PAGE, and does not bind to the 185 kd precursor or to polypeptides of either of Groups 1 or 2.

The results shown in Table 3 indicate that the 185 kd precursor molecule contains at least two distinct antigenic (immunogenic) determinants. They also indicate that the hybridomas of this invention secrete monospecific receptor molecules because there is no cross-reactivity between processing groups.

The receptor molecules secreted by the F18 and F19 hybridomas of the present study were also examined for their malarial strain specificity by IFAT. Those results, also shown in Table 3, indicate that while two monoclonal antibodies may have the same processing group specificity, as described above, they can also recognize different antigenic determinants within a group.

For example, hybridomas F19-P21-9C and F19-P5-11D both produce receptors that recognize the Group 2 185 kd processing polypeptides (152 kd, 106 kd and 83 kd). However, while the antigenic determinant recognized by F19-P21-9C receptors was present in all five strains of *P. falciparum* assayed, the determinant recognized by F19-P5-11D was present in only the Honduras and Geneva strains.

These results are important for vaccine design because they indicate the presence of at least one antigenic determinant common to the five important *P. falciparum* strains studied. Thus, to have broad spectrum effectiveness, an active vaccine should incorporate immunogenic determinants similar to those with which the receptors of the hybridomas of this invention such as hybridoma F19-P21-9C react.

In addition, these results also indicate the presence of strain specific determinants. Such determinants may be important in epidemiological studies where the source of a malarial outbreak must be identified. Clinically, strain-specific determinants may also be important in identifying drug-resistant strains of malaria.

The antibodies secreted by the hybridomas of the present invention may therefore be used as a diagnostic aid by screening a patient's erythrocytes to determine if antigens characteristic of a *P. falciparum* merozoite are present. For example, receptors produced by hybridoma F19-P21-9C may be first used in an IFAT or other assay to show the presence of infection due to the Honduras, Kenya, Indonchina, Geneva or Tanzania strains. Thereafter, a similar analysis using receptors from hybridomas F18-P3-10G or F18-P2-10E may be used to exclude the Kenya, Indochina and Tanzania, or Honduras and Tanzania strains respectively.

Once the presence of an infection due to a particular strain has been identified by use of the above technique to identify the presence of its particular, strain-specific antigen, the patient may be treated with standard drug therapy. The patient may also be treated in a passive immunization procedure with a preparation that contains an effective amount of receptor molecules of this invention in a physiologically tolerable diluent such as normal saline or phosphate-buffered saline. The receptor molecules utilized may be relatively specific for the particular parasite strain such a those produced by hybridomas F18-P3-10G or F19-P9-11B. The patient may also be treated by a similar passive immunization procedure using receptor molecules such as those produced by hybridoma F19-P21-9C or F19-P17-6E that imunoreact with each of the five parasite strains.

II. MATERIALS AND METHODS

A. Monkeys

During the past ten years, an increasing amount of research has shown not only that some Plasmodia of monkeys or apes can be transmitted to man, but also that human malaria parasites can be successfully transmitted to some lower primates and especially to several species of neotropical monkeys. Thus, *P. vivax, P. falciparum* and *P. malaria* can now be transmitted by Anopheles to the Columbian Night or Owl monkey *Aotus trivirqatus*. The monkeys utilized in this study were obtained from the colony of *Aotus trivirgatus* located at the Scripps Clinic and Research Foundation, La Jolla, Calif.

B. MONKEY LYMPHOCYTES

The hybridomas and monoclonal receptor molecules of this invention may be obtained by fusing the lymphocytes of an immunized Aotus with myeloma cells. In the present study, immunized B lymphocytes that secreted receptor molecules were obtained from *Aotus trivirgatus* monkeys that had been infected with the *Plasmodium falciparum* isolate designated FVO obtained originally from Vietnam. We obtained the FVO isolate from Dr. William Collins of The Center for Disease Control (CDC), Atlanta, Ga. The five strains of *P. falciparum* shown in Table 3 were also obtained form Dr. Collins.

1. Propagation of *Plasmodium falciparum*

*Plasmodium falciparum* FVO isolate was grown in vitro using the candle jar method of Tragar and Jensen (1976) *Science* 193:673–75. Briefly, human type O positive erythrocytes were suspended to a 5% hematocrit in RPMI-1640 medium (Irvine Scientific, Irvine, Calif.) and 10% human type 0 positive serum, 40 micrograms (ug)/microliter gentamycin and 25 millimolar (mM)

HEPES buffer. The infected erythrocyte cell cultures were propagated in 100×15 millimeter (mm) petri dishes (Scientific Products) held in a candle jar with the medium, 10 milliliters (ml), changed manually once a day.

A "candle jar" is a dessicator equipped with a stop cock in which a white candle has been centrally placed. The candle is lit after the petri dishes have been placed in the dessicator, and the cover is put on with the stop cock open. When the candle goes out the stop cock is closed. This process produces an atmosphere with a low $O_2$ and a high $CO_2$ content within the candle jar. The petri dishes were then incubated at 37 degrees centigrade.

Fresh medium was provided daily by gently tipping the dishes, withdrawing the supernatant fluid and replacing it with a portion of fresh RPMI-1640 medium as described above. Fresh erythrocytes were added every third or fourth day. Segmentors and free merozoites were harvested, washed twice with RPMI-1640 medium supplemented as described before, and were frozen and thawed three times prior to use in lymphocyte stimulation.

*Plasmodium falciparum* may also be propagated in vivo. In the present study, an *Aotus trivirgatus* monkey designated Aotus 27 was infected with *P. falciparum* by intravenous injection (i.v.) of the FVO isolate. Parasitemic blood from Aotus 27 was used to infect Aotus 33. Aotus 33 was infected by i.v. injection on Sept. 1, 1982. On Sept. 10, 1982 Aotus 33 showed a 13% parasitemia.

2. In Vivo Antiqenic Stimulation

Preferred embodiments of the methods of preparing the hybridomas and receptor molecules of this invention include a process for enriching the lymphocytes for receptor molecule production. In the present study, the in vivo enrichment process was performed on an *Aotus trivirgatus* monkey desigated Aotus 127 (Karyotype II).

Aotus 127 was first immunized by infection with *P. falciparum* on May 14, 1982. The infection was accomplished by the intravenous injection of 0.09 ml packed cell volume (PCV) of infected erythrocytes obtained from Aotus 27 suspended in 1 ml of RPMI-1640 medium. On May 20, 1982 Aotus 127 was patent, but on May 26, and May 30, 1982 Aotus 127 exhibited a 2% parasitemia.

On June 7, 8 and 9, 1982 Aotus 127 received the following drug treatment: Daraprim 0.65 milligrams (mg) all three days and Leucoborin 1.5 mg on June 7, 1982, 0.5 mg on June 8, 1982 and 0.5 mg on June 9, 1982.

On Sept. 1, 1982 the initial intravenous injection of Aotus 27 blood was repeated. On Sept. 10, 1982 1.1 ml PVC of Aotus 33 blood exhibiting a 13% parasitemia was injected intravenously into Aotus 127.

Approximately one year later, and three days before receptor molecule-producing lymphocytes were harvested by spleenectomy, the lymphocytes were antigenically stimulated in vivo by intraperitoneally injecting Aotus 127 with 0.2 ml of the frozen and thawed parasite material described before, diluted to 1 ml in RPMI-1640 medium.

Thereafter, the spleen was removed aseptically, and was gently teased apart. The splenocytes were washed with cold phosphate-buffered saline [PBS; 150 mM NaCl and 10 mM $Na_2PO_4$ (pH 7.4)] and were frozen in 10% DMSO, 50% RPMI-1640 medium and 40% fetal calf serum (FCS). For fusions, one vial of splenocytes containing about $5–10 \times 10^6$ cells was rapidly thawed, the cells were washed with Dubecco's high glucose medium and were immediately fused, as discussed hereinafter.

3. In Vitro Antiqenic Stimulation

In another preferred embodiment of the method of producing the hybridomas and receptor molecules of this invention, the receptor molecule-producing lymphocytes were enriched by in vitro antigenic stimulation. The lymphocytes antigentically stimulated in vitro in the present study were obtained from an *Aotus trivirgatus* monkey designated Aotus 37 (Karyotype VI).

Aotus 37 was initially immunized by infection with *P. falciparum* isolate FVOc, a non-knob-forming isolate derived from isolate FVO, also obtained from Dr. Collins. Initial infection was accomplished by i.v. injection of 1.2 ml PCV FVOc-infected erythrocytes (7% parasitemia) suspended in 1.8 ml RPMI-1640 medium on Oct. 4, 1980. On October 22, 1980 Aotus 37 demonstrated a peak parasitemia of 0.7%.

On Nov. 24, 1981, Apr. 26, 1982 and Sept. 1, 1982, Aotus 37 was boosted with 0.09 ml PCV of Aotus 27 blood having a 10% parasitemia in 1 ml of RPMI-1640 medium. On Sept. 10, 1982, Aotus 37 was boosted with an intravenous injection of 1.1 ml PVC Aotus 33 blood having a 13% parasitemia as described above. About one year later, receptor-producing lymphocytes were harvested by drawing 7 ml of blood by vena puncture, using heparin as an anticoagulant.

The receptor-producing, peripheral B lymphocytes (PBL) were isolated from the blood of the immunized simian in the following manner: The 7 ml of Aotus 37 blood was admixed with an equal volume of PBS. Aliquots containing 5 ml of the admixture were layered over 10 ml of Ficoll Hypaque in a 50 ml Corning centrifuge tube. The overlays were spun at 2,000 rpm for 20 minutes in a Sorval RT 6000 centrifuge using a Sorval H 1000 rotor at 20° C. After centrifugation, the top layers were aspirated off and the B lymphocyte-containing interfaces were recovered and pooled. Enough PBS at 0° C. was then added to the pool to make a total volume of 15 ml.

The cells were washed twice by centrifugation at 1500 rpm for 10 minutes at 0° C. The pellets were collected, were resuspended in 1 mls PBS, and were centrifuged as before. Approximately $2 \times 10^7$ cells were suspended for four days in 10 ml of Dulbecco's high glucose medium supplemented with 10% fetal bovine serum, $5 \times 10^{-5}$ molar (M) 2-mercapto ethanol (2-ME) and 40 microliters of frozen and thawed parasitized erythrocytes obtained by candle jar cultivation as described before. The surviving PBL, about $1 \times 10^7$ cells, were washed and fused with myeloma cells as discussed hereinafter.

C. Myeloma Cells

The mouse myeloma cell lines designated P3X63Ag8.653 (ATCC CRL 1580) and P3X63Ag8 (ATCC TIB 9) were adapted to and subsequently grown in Dulbecco's high glucose medium (Irvine Scientific) supplemented with 10% heat-inactivated gamma globulin-free horse serum (Gibco, Grand Island, N.Y.). The cells were subcultured daily to $4 \times 10^5$ cells per ml for at least 3 days prior to any cell fusion studies.

D. Fusions and Monoclonal Antibody Secretion

Hybridomas of this invention were formed by the fusion of simian receptor-producing B lymphocytes with myeloma cells. Fusions were accomplished by admixing the lymphocyte and myeloma cells in the presence of a fusion promoter such as Sendai virus, polyethylene glycol (of molecular weight of about 500 to about 2000) or an electric current.

In the present study, fusions using either in vivo or in vitro antigenically stimulated B lymphocytes were performed in the same manner. Approximately $1 \times 10^7$ lymphocytes were admixed with an approximately equal number of myeloma cells in 50 ml of Dulbecco's serum-free medium. The cells were pelleted by centrifuging for 10 minutes at 1500 rpm in a Sorvall RT 6000 centrifuge using a Sorval H 1000 rotor. The resulting supernatant was aspirated off, and the pellet was agitated so as to disperse the cells.

To the cells, were added 1 ml of the fusion promoter consisting of out gassed RPMI-1640 medium containing 35% weight by volume polyethylene glycol 1000 [polyoxyethylene (20)]and 7.5% volume by volume DMSO. This solution was added slowly over approximately 1 minute while keeping the cells agitated. Over the next minute, 1 ml of HAT medium (Dulbecco's high glucose medium containing 10% heat-inactivated gamma globulin-free horse serum, 0.1 mM hypoxanthine, 0.001 mM aminopterin and 0.03 mM thymidine) were admixed with the cells. Over the next minute, another 1 ml of HAT medium was slowly added. Subsequently, another 8 ml of HAT medium were added over the next 2 minutes.

The cells were then pelleted by centrifugation at 1500 rpm for 10 minutes, as previously described. After discarding the supernatant, the cells were gently resuspended in 10 ml of HAT medium, and were added to 400 ml HAT medium containing thymocytes, as described hereinbelow. The cells were seeded into 96 well tissue culture plates (Costar) by adding 200 microliters (ul) of HAT medium-containing cells to each well and were cultured.

Fusions using in vivo antigenically stimulated lymphocytes were initially plated at a density of approximately $5 \times 10^3$ cells per well (200 ul). Fusions using in vitro antigenically stimulated lymphocytes were plated at an initial concentration of about $1.5 \times 10^4$ cells per well (200 ul). Mouse-mouse fusions were plated at an initial density of $8 \times 10^4$ cells per well (200 ul). The fused cells were then cultured in a humidified atmosphere containing 7% $CO_2$ at 37° C.

Fusions using monkey lymphocytes were fed on days 7 and 15 after fusion by removing 100 microliters of supernatant from each well and replacing it with 100 microliters of fresh HAT medium containing Balb/c ByJ mouse thymocytes as a feeder layer. On day 21 after fusion, and weekly thereafter, the cultures were fed HAT medium without thymocytes. Mouse fusion cultures were fed with fresh HAT medium containing Balb/c ByJ mouse thymocytes on day 7 after fusion and once a week thereafter with fresh HAT medium without thymocytes.

Balbc/ByJ mouse thymocytes were prepared by teasing the thymuses of 5 Balbc/ByJ mice into 10 ml of Dulbecco's medium. The thymocytes were pelleted by centrifugation for 10 minutes at 1500 rpm in the Sorval centrifuge and rotor described before. After being washed twice by resuspension and pelleting in 10 ml of Dublecco's medium, the thymocytes were resuspended in 400 ml of Dulbecco's medium supplemented as appropriate for either seeding or feeding as described before.

E. Immunofluorescent Antibody Test (IFAT)

1. Assay Procedure

The presence of Aotus monoclonal antibodies specific for *P. falciparum* merizoite antigens was determined by IFAT. Briefly, 100 microliters (ul) of supernatant from a 96 well culture were added to 100 ul of PBS. 10 Microliters of the diluted supernatant were incubated on a merozoite-containing test (IFAT) slide for 30 minutes at room temperature. The IFAT slide was then washed two times with PBS, two times with distilled water, and was allowed to air dry at room temperature.

Aotus anti-merozoite antibodies bound to merozoite antigens on the slide were immunoreacted with 10 ul of fluorescein isothiocyanate (FITC)-labeled rabbit anti-Aotus immunoglobulin antiserum for 30 minutes at room temperature. The slides were again washed two times with PBS, two times with distilled water and allowed to air dry. Slides were then examined by fluoresceant microscopy to assay for the presence of Aotus anti-merozoite antibodies bound to merozoite antigens attached to the slides.

The IFAT titers noted in connection with the before-discussed Tables are the reciprocal of the largest hybridoma supernatant dilution at which a positive assay result could be obtained. Dilutions were carried out by factors of three. Thus, the titers of Table 1 are shown in powers of three; i.e., 3,9,27 and 81.

The strain specifities shown in Table 3 for the receptor molecules produced by the hybridomas were determined by the approximate percentage of fluorescent merozoites that was observed in the microscope field. Test slides whose fields showed that about 75 percent or more fluorescing merozoites were counted as positive (+); slides whose fields showed about 20 percent or fewer fluorescing merozoites were counted as negative (−); while the single assay shown as equivocal (±) had a fluorescing merozoite percentage of between about 20 and about 75 percent.

2. Rabbit Anti-Aotus FITC Conjuqate

FITC-labeled rabbit anti-Aotus immunoglobulin (Ig) antibodies were prepared by methods well known in the art. Briefly, a rabbit was immunized, boosted twice with 0.2 ml of Aotus serum, and was subsequently bled. Approximately 11 ml of rabbit anti-Aotus Ig were obtained by a 50% saturated ammonium sulfate precipitation (45 mg protein per ml) of the immunized rabbit serum.

The rabbit anti-Aotus Ig antiserum thus obtained was affinity purified using an Aotus Ig-CNBr Sepharose 4B (Pharmica Fine Chemicals, Piscattaway, N.J.) column. The bound rabbit anti-Aotus Ig antibody was eluted with 0.2 M glycine, 0.15 M NaCl buffer (pH 2.26). The Ig fractions (optical density of about 2.0) were pooled (approximately 35 ml), concentrated to 5 ml using an Amicon concentrator with PM30 filters (Amicon Corporation, Danvers, Mass.), and dialized against 0.85% NaCl.

The approximately 3.3 ml of rabbit antibodies recovered from dialysis were neutralized with 0.37 ml of 0.5 M carbonate buffer (pH 9.5) and fluorescein isothiocyanate (FITC)-labeled by dialysis against 2.3 mg of FITC in 55 ml of buffer (0.05 M carbonate, 0.85% NaCl, pH 9.5) for 18 hours. The resulting rabbit anti-Aotus Ig-FITC conjugate was used in the IFAT described before at a 1:20 dilution in PBS.

F. Radioimmune Precipitation Assay (RIPA)

Merozoite proteins were metabolically labeled as follows. Briefly, merozoite candle jar cultures were grown as described hereinabove, but were supplemented with either one millicurie of $^3$H-glucosamine or 1 microcurie of $^3$H-thymidine.

After growing in the presence of either isotope for 18 hours, cultures were harvested by resuspending the erythrocytes in their growth medium, and pelleting them by centrifugation for ten minutes at 2,500 rpm in a Sorval RT 6000 centrifuge using a H 1000 rotor. The cells were washed twice by resuspending the pellets in 10 ml of serum-free Dulbecco's medium. The washed cells were aliquoted for use in the RIPA assay by diluting 50 ul of PCV erythrocytes into 250 ul with PBS. The diluted cells were then aliquoted by placing 50 ul into a tube that was subsequently frozen at −70° C. for storage.

A RIPA was performed by first diluting one of the above-described aliquots into 5 ml of RIPA buffer (150 mM NaCl 1, 1% TRITON X-100 [polyoxyalkylene (9) octyl phenyl ether], 1% sodium deoxycholate, 0.1% sodium dodecylsulfate, 20 mM EDTA, and 10 mM Tris-HCl at pH 7.4 This composition was centrifuged for 45 minutes at 40,000 rpm in a Beckman SW 50.1 rotor. The resulting supernatant was collected and divided into 100 ul aliquots.

The metabolically radiolabeled merozoite proteins were immunoreacted with receptor molecules produced in accordance with this invention as follows. To each of the above described aliquots was added 10 ul of *Staphylococcus aureus* protein A-Sepharose to which monkey anti-merozoite antigen monoclonal antibodies had been covalently linked. The reaction mixture was incubated for one hour with gentle agitation.

The antibody-coated protein A-Sepharose beads were then separated from the reaction mixture by centrifugation for 30 seconds in a Fisher Microcentrifuge. The beads were washed one time with RIPA buffer containing 500 mM sodium chloride and one time with distilled water. The pellets were resuspended in 50 ul of sample buffer [0.0625 M Tris-HCl (pH 6.8), 2% SDS, 10% glycerol, 5% 2-ME and 0.001% bromophenol blue]for one minute. The immunoreaction products were thereafter separated, and analyzed by electrophoresis on a 9% polyacrylamide gel in the presence of sodium dodecylsulfate (SDS-PAGE) as described by Laemmli, 1970, *Nature* 227:680-83. The resulting gels were analyzed by autoradiography using Kodak XRP-1 X-ray film (Kodak, Rochester, N.Y.).

G. Receptor-Antibody Interactions

Studies carried out using antibodies to mouse Ig and human Ig were carried out using commercial preparations of polyclonal FITC-labeled goat antibodies raised against the respective animal type antibodies (Tago, Burlingame, Calif.). Briefly, IFAT test slides were prepared and reacted with receptors of this invention as previously described. The FITC-labeled goat anti-human Ig or anti-mouse Ig antibodies were thereafter admixed with the Aotus antibody-bound merozoites at a 1:50 dilution. The slides were incubated, washed and read as before-described.

The anti-mouse Ig antibodies did not immunoreact with the Aotus receptors of this invention. Receptor molecules from each of hybridomas denominated F18-P3-10G, F18-P2-10E, F19-P9-11B and F19-P21-9C were bound by the goat anti-human Ig antibodies.

The foregoing is intended as illustrative of the present invention but not limiting. Numerous variations and modifications may be effected without departing from the true spirit and scope of the invention.

What is claimed is:

1. A process for preparing Aotus monoclonal receptor molecules that immunoreact with a *Plasmodium falciparum* comprising the steps of:
   (a) collecting antibody-producing cells from *Aotus trivirgatus* immunized by a protein of *Plasmodium falciparum*;
   (b) fusing said cells with cells of a mouse myeloma cell line to form hybridomas, said myeloma cells containing about the same number of chromosomes per cell as do the antibody-producing cells, said fusion being carried out in the presence of a cell fusion promoter;
   (c) cloning said hybridomas in a culture medium selective for hybridoma growth;
   (d) assaying and selecting said cloned hybridomas for the ability to secrete receptor molecules that immunoreact with said predetermined antigen;
   (e) subcloning to monoclonicity a selected hybridoma;
   (f) culturing the selected, subcloned hybridoma of step (e); and
   (g) collecting the monoclonal receptors secreted by said cultured hybridoma of step (f).

2. The process according to claim 1 wherein said myeloma cell line is a non-secreting myeloma cell line.

3. The process according to claim 1 wherein said non-secreting myeloma cell line is the mouse myeloma cell line denominated P3X63Ag8.653.

4. The process according to claim 1 wherein said *Plasmodium falciparum* protein is a protein of a shizont or merozoite.

5. The process according to claim 1 including the further step of enriching said antibody-producing cells by antigenic stimulation within a time period of about one week of their collection for fusion.

6. The process according to claim 5 wherein said antigenic stimulation is carried out in vivo.

7. The process according to claim 1 wherein said antibody-producing cells are splenocytes or peripheral B lymphocytes.

8. The process according to claim 1 including the further steps of freezing said collected antibody-producing cells, and then thawing said frozen cells immediately prior to said fusion.

9. The process according to claim 1 wherein said cloning step is carried out at a concentration of about $4 \times 10^3$ to about $2 \times 10^4$ cells per milliter.

10. A hybridoma cell line produced by the fusion of antibody-producing cells from *Aotus trivirgatus* and cells from mouse myeloma P3X63Ag8.653, said cell line, when cultured, secreting monclonal receptor molecules for a time period of at least six weeks after cloning that:
    (a) immunoreact with a protein of *Plasmodium falciparum*;
    (b) are bound by polyclonal antibodies raised to antibodies of *Aotus trivirgatus*; and
    (c) are not substantially bound by polyclonal antibodies raised to mouse antibodies.

11. The cell line according to claim 10 wherein said antibody-producing cells are splenocytes or peripheral B lymphocytes.

12. The cell line according to claim 10 wherein said receptor molecules are bound by polyclonal antibodies raised to human antibodies.

13. The cell line according to claim 10 wherein said *Plasmodium falciparum* protein is a protein of a shizont or merozite.

14. The cell line according to claim 10 wherein the hybridoma is denominated F18-P3-10G, ATCC HB 8641.

15. The cell line according to claim 10 wherein the hybridoma is denominated F18-P2-10E, ATCC HB 8640.

16. The cell line according to claim 10 whrein the hybridoma is denominated F19-P21-9C, ATCC HB 8643.

17. The cell line according to claim 10 wherein the hybridoma is denominated F19-P9-11B, ATCC HB 8642.

18. *Aotus trivirgatus*-mouse hybridoma-secreted monoclonal receptor molecules that:
    (a) immunoreact with a protein of *Plasmodium falciparum;*
    (b) are bound by polyclonal antibodies raised to antibodies of *Aotus trivirgatus;* and
    (c) are not substantially bound by polyclonal antibodies raised to mouse antibodies.

19. The receptor molecules according to claim 18 wherein said receptor molecules immunoreact with a protein of *Plasmodium falciparum* shizonts or merozoites.

20. The receptor molecules according to claim 18 wherein said protein is a glycoprotein having a molecular weight by SDS-PAGE of about 185 kd that is made by shizonts and is processed into polypeptide fragments during merozoite development.

21. The receptor molecules according to claim 18 wherein said hybridoma is formed by the fusion of antibody-producing cells of an *Aotus trivirgatus* immunized to said *Plasmodium falciparum* protein and a mouse myeloma cells containing about the same number of chromosomes per cell as do said antibody-producing cells.

22. The receptor molecules according to claim 21 wherein said Aotus antibody-producing cells contain 54 or 56 chromosomes.

23. The receptor molecules according to claim 21 wherein said mouse myeloma cells are from the cell line denominated P3X63Ag8.653.

24. A process for preparing an Aotus interspecies hybridoma comprising the steps of:
    (a) collecting antibody-producing cells from *Aotus tirvirgatus* immunized by a protein of *Plasmodium falciparum;*
    (b) fusing said cells with cells of a mouse myeloma cell line to form hybridomas, said myeloma cells containing about the same number of chromosomes per cell as do the antibody-producing cells, said fusion being carried out in the presence of a cell fusion promoter;
    (c) cloning said hybridomas in a culture medium selective for hybridoma growth;
    (d) assaying and selecting said cloned hybridomas for the ability to secrete receptor molecules that immunoreact with said a *Plasmodium falciparum* protein preselected antigen;
    (e) subcloning to monoclonicity a selected hybridoma;
    (f) culturing the selected, subcloned hybridoma of step (e); and
    (g) collecting the hybridoma of step (f).

25. The process according to claim 24 wherein said Aotus antibody-producing cells contain 54 or 56 chromosomes per cell.

26. The process according to claim 25 wherein said myeloma cell contains 58 chromosomes per cell.

27. The process according to claim 24 wherein said myeloma cell line is a non-secreting cell line.

28. The process according to claim 27 wherein said myeloma cell line is the mouse myeloma cell line denominated P3X63Ag8.653.

29. The process according to claim 24 wherein said *Plasmodium falciparum* protein is a protein of a shizont or merozoite.

30. A process for preparing an Aotus interspecies hybridoma comprising the steps of:
    (a) collecting antibody-producing cells from *Aotus tirvirgatus* immunized by a protein of a *Plasmodium falciparum* shizont or merozoite;
    (b) fusing said cells with cells of a mouse myeloma cell line to form hybridomas, said myeloma cells containing about the same number of chromosomes per cell as do the antibody-producing cells, said fusion being carried out in the presence of a cell fusion promoter;
    (c) cloning said hybridomas in a culture medium selective for hybridoma growth;
    (d) assaying and selecting said cloned hybridomas for the ability to secrete receptor molecules that immunoreact with a *Plasmodium falciparum* shizont or merozoite protein;
    (e) subcloning to monoclonicity a selected hybridoma;
    (f) culturing the selected, subcloned hybridoma of step (e); and
    (g) collecting the hybridoma of step (f).

31. The receptor molecules according to claim 18 that are secreted by the hybridoma denominated F18-P3-10G, ATCC HB 8641.

32. The receptor molecules according to claim 18 that are secreted by the hybridoma denominated F18-P2-10E, ATCC HB 8640.

33. The receptor molecules according to claim 18 that are secreted by the hybridoma denominated F19-P21-9C, ATCC HB 8643.

34. The receptor molecules according to claim 18 that are secreted by the hybridoma denominated F19-P-11B, ATCC HB 8642.

* * * * *